US011285300B2

(12) United States Patent
Felkins et al.

(10) Patent No.: US 11,285,300 B2
(45) Date of Patent: Mar. 29, 2022

(54) SYSTEM AND METHOD FOR MANIPULATING AN ELONGATE MEDICAL DEVICE

(71) Applicant: VESATEK, LLC, Irvine, CA (US)

(72) Inventors: Brandon M. Felkins, Half Moon Bay, CA (US); Lawrence J. Green, Santa Ana, CA (US); Russell Roy Lyon, Days Creek, OR (US); David M. Look, Newport Beach, CA (US); Mark Mallaby, San Diego, CA (US)

(73) Assignee: Vesatek, LLC, Irvine, CA (US)

( * ) Notice: Subject to any disclaimer, the term of this patent is extended or adjusted under 35 U.S.C. 154(b) by 303 days.

(21) Appl. No.: 15/235,920

(22) Filed: Aug. 12, 2016

(65) Prior Publication Data

US 2017/0043137 A1  Feb. 16, 2017

Related U.S. Application Data

(60) Provisional application No. 62/204,366, filed on Aug. 12, 2015.

(51) Int. Cl.
*A61M 25/09* (2006.01)
*A61M 25/00* (2006.01)
*A61B 17/00* (2006.01)

(52) U.S. Cl.
CPC .. *A61M 25/09041* (2013.01); *A61M 25/0097* (2013.01); *A61B 2017/00469* (2013.01); *A61M 2025/09116* (2013.01)

(58) Field of Classification Search
CPC ...... A61M 2205/103; A61M 25/09041; A61M 2205/8206; A61M 1/0064; A61B 17/1622; A61B 2017/0046
See application file for complete search history.

(56) References Cited

U.S. PATENT DOCUMENTS 3,748,435 A   7/1973   Reynolds
3,847,140 A   11/1974  Ayella
(Continued)

FOREIGN PATENT DOCUMENTS

CN    1767869 A    5/2006
CN    202654461 U  1/2013
(Continued)

OTHER PUBLICATIONS

PCT International Search Report and Written Opinion for PCT/US2016/046877, Applicant: Vesatek, LLC, Forms PCT/ISA/220, 210, and 237 dated Oct. 28, 2016 (10 pages).
(Continued)

*Primary Examiner* — Scott J Medway
(74) *Attorney, Agent, or Firm* — Blair Walker IP Services, LLC (57) ABSTRACT

A guidewire manipulation device includes a housing configured to be supported by the hand of a user, the housing having a distal end and a proximal end, the housing configured to allow a guidewire to be placed therethrough and extend between the distal end and proximal end, a drive system carried by the housing and configured to drive rotation of the guidewire, and a manual input module carried by the housing, the manual input module configured to allow one or more fingers of the hand of the user to manually stop or slow the rotation of the guidewire while the housing is supported by the hand of the user.

26 Claims, 7 Drawing Sheets

(56) References Cited

U.S. PATENT DOCUMENTS

| | | | |
|---|---|---|---|
| 4,728,876 A * | 3/1988 | Mongeon | A61B 17/1624 320/114 |
| 4,854,325 A | 8/1989 | Stevens | |
| 5,024,029 A | 6/1991 | Abbott et al. | |
| 5,055,109 A | 10/1991 | Gould et al. | |
| 5,125,906 A * | 6/1992 | Fleck | A61M 25/0113 604/171 |
| 5,158,564 A | 10/1992 | Schnepp-Pesch et al. | |
| 5,207,697 A * | 5/1993 | Carusillo | A61B 17/1626 320/115 |
| 5,216,848 A | 6/1993 | Abbott et al. | |
| 5,243,997 A | 9/1993 | Uflacker et al. | |
| 5,263,938 A * | 11/1993 | Orr | A61M 25/09041 604/171 |
| 5,312,412 A | 5/1994 | Whipple | |
| 5,318,529 A | 6/1994 | Kontos | |
| 5,325,868 A * | 7/1994 | Kimmelstiel | A61B 17/22 600/585 |
| 5,366,464 A * | 11/1994 | Belknap | A61B 17/320758 606/159 |
| 5,389,072 A | 2/1995 | Imran | |
| 5,392,778 A | 2/1995 | Horzewski | |
| 5,415,177 A * | 5/1995 | Zadini | A61M 25/0116 600/585 |
| 5,443,078 A | 8/1995 | Uflacker | |
| 5,476,467 A | 12/1995 | Benoist | |
| 5,507,738 A | 4/1996 | Ciervo | |
| 5,524,180 A | 6/1996 | Wang et al. | |
| 5,524,635 A | 6/1996 | Uflacker et al. | |
| 5,553,675 A * | 9/1996 | Pitzen | A61B 17/1628 173/217 |
| 5,601,601 A | 2/1997 | Tal et al. | |
| 5,634,475 A | 6/1997 | Wolvek | |
| 5,660,180 A | 8/1997 | Malinowski et al. | |
| 5,709,661 A | 1/1998 | Van Egmond et al. | |
| 5,735,535 A | 4/1998 | McCombs et al. | |
| 5,766,191 A | 6/1998 | Trerotola | |
| 5,893,857 A | 4/1999 | Shturman et al. | |
| 5,908,395 A | 6/1999 | Stalker et al. | |
| 5,911,722 A | 6/1999 | Adler et al. | |
| 5,981,628 A | 11/1999 | Takamoto et al. | |
| 6,001,112 A * | 12/1999 | Taylor | A61B 17/320758 606/159 |
| 6,027,460 A | 2/2000 | Shturman | |
| 6,096,042 A | 8/2000 | Herbert | |
| 6,165,188 A | 12/2000 | Saadat et al. | |
| 6,179,809 B1 | 1/2001 | Khairkhahan et al. | |
| 6,183,432 B1 | 2/2001 | Milo | |
| 6,348,040 B1 | 2/2002 | Stalker et al. | |
| 6,533,772 B1 | 3/2003 | Sherts et al. | |
| 6,544,231 B1 | 4/2003 | Palmer et al. | |
| 6,551,302 B1 | 4/2003 | Rosinko et al. | |
| 6,554,794 B1 | 4/2003 | Mueller et al. | |
| 6,726,675 B1 | 4/2004 | Beyar | |
| 6,752,800 B1 | 6/2004 | Winston et al. | |
| 6,939,313 B2 * | 9/2005 | Saadat | A61B 5/015 600/587 |
| 7,288,074 B2 | 10/2007 | Swain et al. | |
| 7,473,263 B2 | 1/2009 | Johnston et al. | |
| 7,479,147 B2 | 1/2009 | Honeycutt et al. | |
| 7,615,042 B2 | 11/2009 | Beyar et al. | |
| 7,766,894 B2 | 8/2010 | Weitzner et al. | |
| 7,972,282 B2 | 7/2011 | Clark et al. | |
| 8,142,458 B2 | 3/2012 | Shturman | |
| 8,187,229 B2 | 5/2012 | Weitzner et al. | |
| 8,323,239 B2 | 12/2012 | Bednarek et al. | |
| 8,500,697 B2 | 8/2013 | Kurth et al. | |
| 9,119,941 B2 | 9/2015 | Rollins et al. | |
| 9,119,942 B1 | 9/2015 | Rollins et al. | |
| 9,532,789 B2 * | 1/2017 | Coope | A61B 17/8625 |
| 9,782,215 B2 * | 10/2017 | Haberstich | A61B 17/00234 |
| 2002/0177789 A1 | 11/2002 | Ferry et al. | |
| 2003/0040694 A1 | 2/2003 | Dorros et al. | |
| 2003/0088187 A1 | 5/2003 | Saadat et al. | |
| 2003/0181934 A1 * | 9/2003 | Johnston | A61B 17/162 606/167 |
| 2003/0216760 A1 * | 11/2003 | Welch | A61B 17/22 606/159 |
| 2004/0054322 A1 | 3/2004 | Vargas | |
| 2004/0236214 A1 | 11/2004 | Opie et al. | |
| 2005/0240116 A1 | 10/2005 | Saadat et al. | |
| 2005/0240120 A1 * | 10/2005 | Modesitt | A61M 25/09041 600/585 |
| 2005/0244521 A1 | 11/2005 | Strickland et al. | |
| 2005/0277851 A1 | 12/2005 | Whittaker et al. | |
| 2006/0041245 A1 | 2/2006 | Ferry et al. | |
| 2006/0074442 A1 * | 4/2006 | Noriega | A61M 25/09 606/159 |
| 2006/0111723 A1 * | 5/2006 | Chapolini | A61B 17/1622 606/80 |
| 2006/0184186 A1 | 8/2006 | Noone | |
| 2006/0229587 A1 | 10/2006 | Beyar et al. | |
| 2006/0282150 A1 | 12/2006 | Olson et al. | |
| 2007/0016105 A1 | 1/2007 | Mamourian | |
| 2007/0060879 A1 | 3/2007 | Weitzner et al. | |
| 2007/0167804 A1 | 7/2007 | Park et al. | |
| 2007/0219467 A1 | 9/2007 | Clark et al. | |
| 2007/0225615 A1 | 9/2007 | Chechelski et al. | |
| 2007/0270755 A1 | 11/2007 | Von Oepen et al. | |
| 2008/0097465 A1 | 4/2008 | Rollins et al. | |
| 2008/0119824 A1 | 5/2008 | Weitzner et al. | |
| 2008/0255539 A1 | 10/2008 | Booth | |
| 2009/0082722 A1 | 3/2009 | Munger et al. | |
| 2009/0105645 A1 | 4/2009 | Kidd et al. | |
| 2009/0264940 A1 * | 10/2009 | Beale | A61B 5/04001 606/86 R |
| 2010/0174233 A1 | 7/2010 | Kuban et al. | |
| 2010/0204613 A1 * | 8/2010 | Rollins | A61M 25/09041 600/585 |
| 2010/0217275 A1 | 8/2010 | Carmeli et al. | |
| 2012/0078080 A1 | 3/2012 | Foley et al. | |
| 2014/0243734 A1 | 8/2014 | Eubanks et al. | |
| 2014/0263542 A1 * | 9/2014 | Leimbach | A61B 17/064 227/175.2 |
| 2014/0324026 A1 | 10/2014 | Chrisman | |
| 2014/0343527 A1 | 11/2014 | Scarpine et al. | |
| 2015/0051584 A1 | 2/2015 | Korkuch et al. | |
| 2015/0202414 A1 | 7/2015 | Hwang | |
| 2017/0151421 A1 * | 6/2017 | Asher | A61M 25/1002 |

FOREIGN PATENT DOCUMENTS

| | | |
|---|---|---|
| EP | 0442137 | 2/1996 |
| JP | H03-5635 | 8/1992 |
| WO | WO 03/079911 A1 | 10/2003 |
| WO | WO 2010/033629 A1 | 3/2010 |

OTHER PUBLICATIONS

SeaDragonTM Torque Device Instructions for Use, Merit Medical, downloaded from internet Aug. 10, 2016 (1 page).

SeaDragonTM One Touch Control, Merit Medical, downloaded from internet Aug. 10, 2016 (2 pages).

Extended European Search Report dated Jul. 5, 2018, in EP App. No. 16836001.4 filed Aug. 12, 2016 (9 pages).

* cited by examiner

SYSTEM AND METHOD FOR MANIPULATING AN ELONGATE MEDICAL DEVICE

INCORPORATION BY REFERENCE TO ANY PRIORITY APPLICATIONS

This application claims the benefit of priority to U.S. Provisional Application No. 62/204,366, filed on Aug. 12, 2015, which is incorporated in its entirety by reference herein for all purposes. Priority is claimed pursuant to 35 U.S.C. § 119.

FIELD OF THE INVENTION

The field of the invention generally relates to devices for manipulating a guidewire or other elongate medical device.

BACKGROUND

The present disclosure generally relates to the maneuvering of a guidewire in medical procedures where an endovascular technique is employed to access vasculature of a patient. A guidewire is typically an elongate probe used as an initial access point for performing an endovascular procedure. The guidewire is twisted ("torqued"), flexed, bent, and otherwise maneuvered through an access vessel in order to position the guidewire tip at or near a location a user (physician, interventionalist, etc.) would like to treat.

Convention guidewire manipulation methods often involve applying "torque" to the guidewire to aid its passage through tortuous and clogged vessels. This maneuver is performed by quickly and stiffly spinning the wire in one's fingertips. This torque helps curve or manipulate the guidewire through an obstruction or difficult passageway. This technique is also known as "helicoptering", alluding to the spinning blades of a helicopter.

However, applying torque remains difficult because guidewires are extremely thin in diameter and typically have a low friction surface. Additionally, the gloves of a user are often coated with blood or saline solution, further increasing the slackness of the guidewire. In this respect, helicoptering and similar maneuvers can be time consuming and inefficient. This inefficiency not only frustrates users but also increases procedure times and therefore procedure costs.

Present guidewire designs attempt to address these problems by providing a torque handle (torquer) that slips over the proximal end of the guidewire and looks in place. The user manipulates this torque device to facilitate rotational motion of the guidewire and grip.

These current techniques and practices have several problems. First, the current torque devices require a user to concentrate on spinning the guidewire with the attached torque device. The spinning technique greatly depends on the ability of the user and can be difficult to learn. Thus, these devices remain inefficient and often highly dependent on the operator skill. Because it is highly desirable to place a guidewire quickly and therefore finish a procedure quickly, a more consistently controllable guidewire placement device that overcomes these disadvantages is desired. This is also true of other, non-guidewire, elongate medical devices that may be used for an interventional procedure.

SUMMARY OF THE INVENTION

In a first embodiment of the invention, a guidewire manipulation device includes a housing configured to be supported by the hand of a user, the housing having a distal end and a proximal end, the housing configured to allow a guidewire to be placed therethrough and extend between the distal end and proximal end, a drive system carried by the housing and configured to drive rotation of the guidewire, and a manual input module carried by the housing, the manual input module configured to allow one or more fingers of the hand of the user to manually stop or slow the rotation of the guidewire while the housing is supported by the hand of the user.

In another embodiment of the invention, a method for manipulating an elongate medical device includes providing a guidewire manipulation device including a housing configured to be supported by the hand of a user, the housing having a distal end and a proximal end, the housing configured to allow a guidewire to be placed therethrough and extend between the distal end and proximal end, a drive system carried by the housing and configured to drive rotation of the guidewire, and a manual input module carried by the housing, the manual input module configured to allow one or more fingers of the hand of the user to manually stop or slow the rotation of the guidewire while the housing is supported by the hand of the user, securing an elongate medical device to at least a portion of the guidewire manipulation device, grasping the guidewire manipulation device in a hand, and causing the elongate medical device to change a rotation speed by input from one or more finger of the hand.

DETAILED DESCRIPTION

The present disclosure includes embodiments of systems for manipulating elongate medical devices, such as guidewires, thrombectomy devices, including brushes, beaters, rooter-type apparatus, drills, or atherectomy devices. Standard guidewires range from 0.009 inches (0.229 mm) in diameter to 0.038 inches (0.965 mm) in diameter. Guidewires for use in coronary arteries are often between about 0.010 inches (0.254 mm) and about 0.018 inches (0.457 mm). The systems for manipulating elongate medical devices may be configured to lock onto and rotate the elongate medical device on one direction or in two different directions. The systems for manipulating elongate medical devices may instead (or also) be configured to longitudinally displace, or piston, the elongate medical device backward and forward (proximally and distally). A number of different speeds may be used, depending on the particular material being acted upon.

Some embodiments presented in the present disclosure are designed to clamp or otherwise engage onto a guidewire, including standard guidewire diameters, in order to provide rotational motion thereto. Rotational motion is one particular mode of manipulation, however, the systems presented in the embodiments could also be used to increase pushability or trackability of a guidewire. In additional, an oscillating linear motion may be incorporated into the systems. Once the system for manipulating a medical device is engaged with the guidewire, the system will be capable of being activated to rotate the guidewire in one or both of a clockwise (CW) direction and a counter-clockwise (CCW) direction. In addition, the speed of rotation (e.g., revolutions per minute) may be adjusted by the user with a control knob carried by the system. In some embodiments, the system comprises a handle having a "reverse gun handle" shape, which, among other things, allows one or more fingers of the user to have access to one or more control elements (buttons, knobs, etc.) without having to regrip the handle. The system may also be configured to allow the user to apply manual input. For example, the rotation of the guidewire which is applied by the system may be slowed down or completely stopped by manual input from one or more fingers of the user. For clarity purposes, the thumb is considered a finger, as are the other digits of the hand. When discussing a finger herein, for example a finger that is contacting a surface, it is intended to encompass both an uncovered finger and a covered (e.g., gloved) finger. The system may also be configured to allow the user to apply manual input via one or more fingers, to impart rotation on a non-rotating guidewire, or to increase rotation speed of a rotating guidewire.

Figure 1:
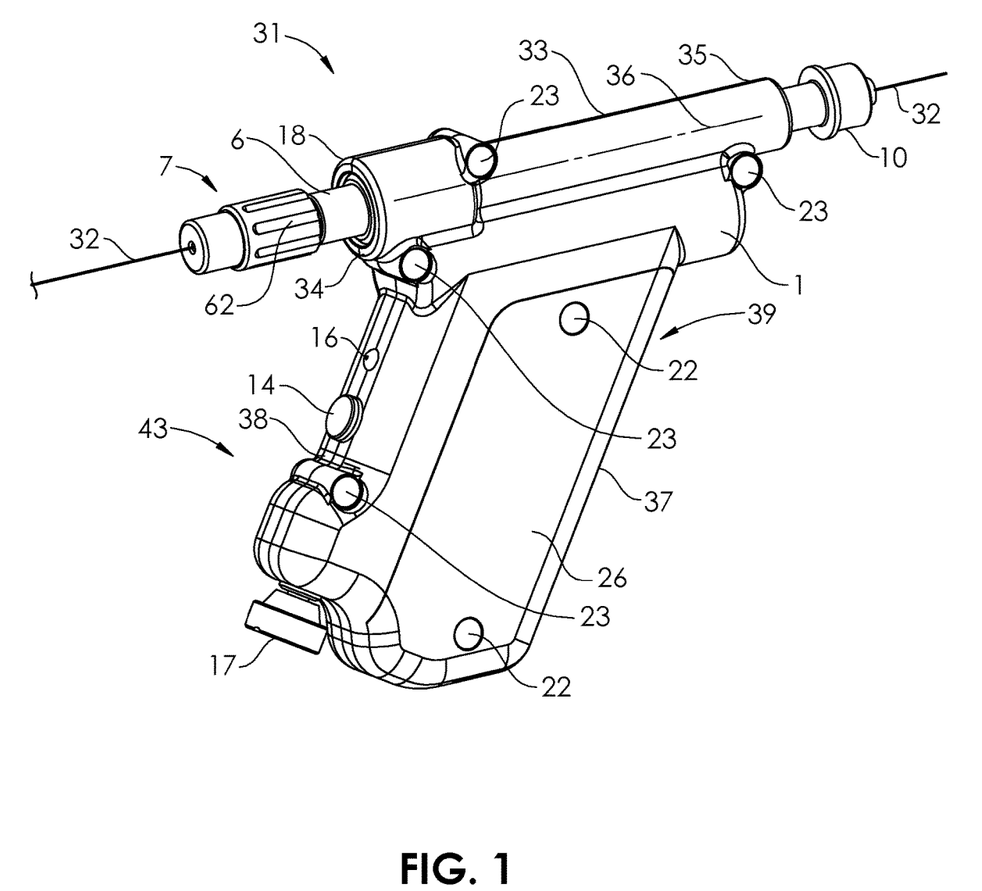
FIG. 1 is a perspective view of a guidewire manipulation device according to a first embodiment of the disclosure.
Figure 2:
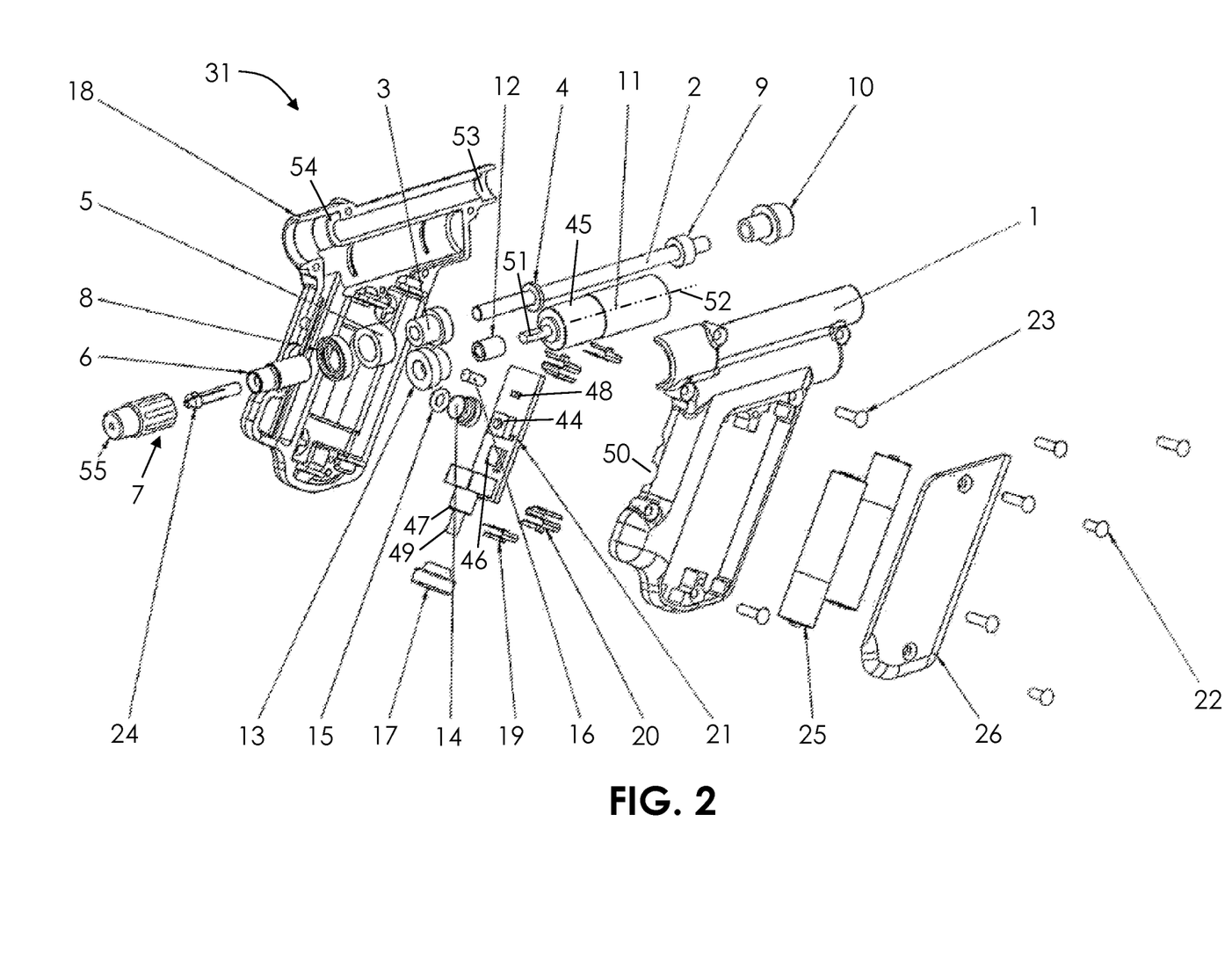
FIG. 2 is an exploded view of the guidewire manipulation device of FIG. 1.

A first embodiment of a guidewire manipulation device 31 is illustrated in FIGS. 1-4. A housing 33 includes a first housing half 1 and a second housing half 18, which are configured to hold a number of components, and to provide an interface with the hand of a user. The first housing half 1 and the second housing half 18 are secured to one another by screws 23. The housing 33 has a distal end 34 and a proximal end 35 and a longitudinal axis 36 though which a guidewire 32 may be placed, to extend between the distal end 34 and the proximal end 35. A chuck 7 is rotatably mounted on the housing 33 and is configured to releasably engage a guidewire. The chuck 7 has an unlocked mode in which it is not engaged with the guidewire 32, and thus the guidewire 32 can be slid longitudinally with respect to the housing 33 and the chuck 7. The chuck 7 also has a locked mode in which it is engaged with the guidewire 32, thus maintaining the longitudinal position of the guidewire 32 in relation to the housing 33 (and in relation to the chuck 7). In the locked mode, the guidewire 32 and the chuck 7 are rotationally coupled, and can be rotated together, in relation to the housing. Turning to FIG. 2, One or more batteries 25 are held within the housing 33 and covered by a battery cover 26, which is secured to the first half 1 of the housing 33 with screws 22. Two positive contacts 19 or terminals, and two negative contacts 20 or terminals, are held within one or both halves 1, 18 of the housing 33 such that the batteries 25 (two are shown in this embodiment) electrically couple with the contacts 19, 20. The contacts 19, 20 are electrically coupled to a circuit board 21 by conductor wires (not shown), for example, by soldering, or other comparable methods. The circuit board 21 includes an on/off switch 44, which is configured to provide power to a motor 11. The motor 11 is also electrically coupled to the circuit board 21 by standard methods. The motor 11 may be a standard or brushless electric motor, and may include a gear module 45. The motor 11, may also be configured to serve as a stepper motor, whose particular rotational orientation is controlled by a controller 46 on the circuit board 21. The motor 11 may include a thermally insulative and/or physically protective covering disposed over a portion of its outer surface. In some embodiments, the covering may comprise Kapton® (polyimide) tape. In some embodiments, the speed of the motor 11 may be varied by a potentiometer 47. When the motor 11 is activated (e.g., by the on/off switch 44), the circuit board 21 lights an LED (light emitting diode) 48, which is thus configured to indicate motor activity. The LED may be a green color to provide a feeling of "on" to the user, but other colors may be used. The motor 11 rotates the guidewire, reducing the physical requirements on the user, who otherwise would only be able to rotate the guidewire manually, and would thus likely to be subject to fatigue.

A handle 37 extends in a generally radial direction in relation to the longitudinal axis 36. In the embodiment of FIGS. 1-4, the handle 37 includes a distally facing surface 38 and a proximally facing surface 39. Generally, at least a portion of the proximally facing surface 39 is configured to either rest within a portion of the palm of the hand, or at least to be adjacent to the portion of the palm of the hand between the thumb and the index finger. In some cases, the user may grip the handle 37 such that the proximally facing surface 39 is cradled or cushioned within the fleshy portion of the hand between the thumb and the index finger. The guidewire manipulation device 31, including the handle 37, is configured to fit at least partially in the hand of the user in order to allow complete operation of the guidewire manipulation device 31 by this single hand. Generally, at least a portion of the distally facing surface 38 is configured to provide one or more controls 43, and to allow access for the ends of one or more finger of the user's hand. The controls 43 may include an activation button 14 and a control knob 17. The activation button 14 extends from the housing 33 on one side and engages with the on/off switch 44 at the other side, such that the user may operate the on/off switch 44 by pressing the activation button 14 while holding the handle 37 in one hand. An o-ring 15 may be carried by the activation button 14 within a circumferential groove on the outer perimeter of the activation button 14, so that it seals within a hole 50 in the housing 33, to keep external contamination (water, dirt, etc.) from entering the housing 33. The hole 50 is shown in FIG. 2 as comprising two semi-circular holes in each of the two housing halves 1, 18 which come together to make a circular hole. A light pipe 16 is attached to the housing 33 with an external portion on the outside of the housing 33 and an internal portion adjacent the LED 48 of the circuit board 21. The activity of the motor 11 is thus visible by the user, as the light pipe 16 is illuminated via the LED when the motor 11 is in operation. The control knob 17 may be configured to select two or more different rotational settings. For example, the controller 43 of the circuit board 21 may include different routines for rotating a guidewire (eight rotations in one direction, followed by eight rotations in the opposite direction, repeated, etc.). This will be subsequently discussed in more detail. Alternatively, the control knob 17 can be rotationally coupled with the rotatable portion 49 of the potentiometer 47, such that the user may turn the control knob 17 with one or more finger of the hand that grips the handle 37, to change the speed of the motor 11, and thus increase or decrease the rotational speed of the guidewire 32.

Some rotation speeds that may be used include a rotation speed that is adjustable between about 1,000 RPM (rotations per minute) and about 10,000 RPM. In other embodiments, the rotation speed may be adjustable between about 2,000 RPM (rotations per minute) and about 5,000 RPM. Individual exemplary rotation speeds may include 2,500 RPM or 4,000 RPM, but may include higher or lower rotational speed settings, depending on the medical application, and the type of elongate medical device being rotated by the guidewire manipulation device 31. Other controls 43 may include a mode control, which may be configured to switch the motor 11 (e.g., via the controller 46) into different rotational modes, which may include simple continuous rotation in a single rotational direction, back and forth rotation, or stop and start of rotation in a particular rotational direction. The controller 46 may comprise a microcontroller.

The motor 11 is coupled to the chuck 7 as follows. An output shaft 51 of the motor 11 is rotationally coupled to a sleeve 12 onto which a drive gear 13 is press fit or bonded (adhesive, epoxy, hot melt, heat fused). The motor 11, output shaft 51, sleeve 12, and drive gear 13 all have a motor axis 52. A driven gear 3 is carried by the housing 33 and is rotatable around the longitudinal axis 36. The driven gear 3 is configured to mesh with and be driven by the drive gear 13. In some embodiments, a lubricant may be used between the drive gear 13 and the driven gear 3. Some potential lubricants include Krytox® or silicone oil. In the embodiment of FIG. 2, the motor axis 52 is substantially parallel and non-co-linear with the longitudinal axis 36. In alternative embodiments, the motor axis 52 may be angled in relation to the longitudinal axis 36, for example, if bevel gears are used. The driven gear 3 is rotationally coupled to a rotatable drive tube 2, which rotates around the longitudinal axis 36. The drive tube 2 is rotationally held and maintained longitudinally within the housing 33 by a bearing 9 and a spacer 4. The bearing 9 is held within a cavity 53 and the spacer abuts a flange 54. The driven gear 3 abuts a bearing 5. The word "chuck" is intended to broadly describe any component which is capable of gripping or holding a guidewire 32 or other elongate medical device. The chuck 7 of FIGS. 1-4 is rotationally coupled to the drive tube 2 and includes a collet holder 6, a collet 24, and a compression cap 55, which is threadingly coupled to the collet holder 6. When the compression cap 55 is tightened to the collet holder 6, the collet 24 is forced closed, gripping the guidewire. The compression cap 55 includes a gripping portion 62. The gripping portion 62 may alternatively be carried on any other external surface of the chuck 7. The collet 24 may be made from brass, bronze, or other metals which do not unacceptably damage the guidewire 32 (or other elongate medical devices). A seal 8 serves to seal the collet holder 6 within the housing 33 even as the collet holder 6 rotates. A luer lock 10 is bonded to the housing 33 or the drive tube 2, and may be used to couple a syringe (with or without an extension tube), so that the interior of the housing around the guidewire 32 may be flushed prior to, after, or during a medical procedure. Though a male luer lock is shown in FIGS. 1-4, alternatively, a female luer lock or a non-locking male or female luer may be used. Though the guidewire 32 is shown in FIGS. 1 and 4 extending a small amount proximally from the housing 33, in use, the guidewire need not extend at all.

Alternatively, the luer lock 10 may be attached to the drive tube 2 instead of the housing 33, for example at the distal end of the drive tube 2, in order to be rotated by the drive tube 2. In this embodiment, the luer lock 10 is configured to be coupled to the proximal luer hub of a catheter, which may include a microcatheter, or a sheath. The motor 11 may then be configured to rotate the catheter or sheath to allow the distal end of the catheter or sheath to more easily be tracked through tortuous vasculature, or through an occlusion or stenosis. The catheter or sheath may also be operated as a drilling member or coring member to cannulate a thrombus or lesion. In the tracking application, the rotational speed setting may even be significantly less than 1,000 RPM, and in the drilling operation, the rotational speed may even be greater than 10,000 RPM.

The handle 37 may have a first side 41 and a second side 42 extending between the distally facing surface 38 and the proximally facing surface 39. In some embodiments, both sides 41, 42 may be substantially flat, and in other cases, both sides 41, 42 may have contour or curvature, such that the handle 37 may be usable by either a left hand or a right hand. In other embodiments, the one of the two sides 41, 42 may have a different shape than the other of the two sides 41, 42, which may be done in order to provide either a left hand only device or a right hand only device.

Figure 3:
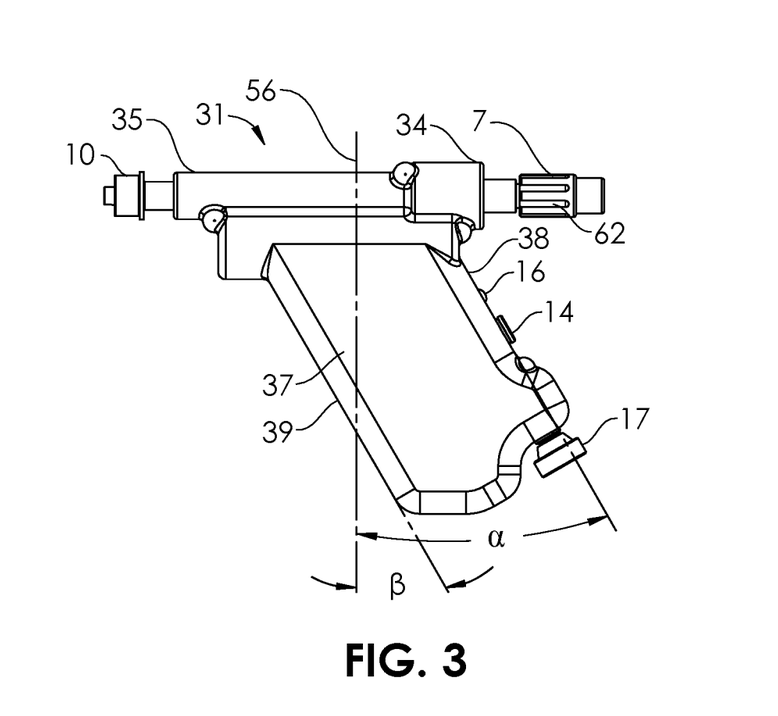
FIG. 3 is a side view of the guidewire manipulation device of FIG. 1.
Figure 4:
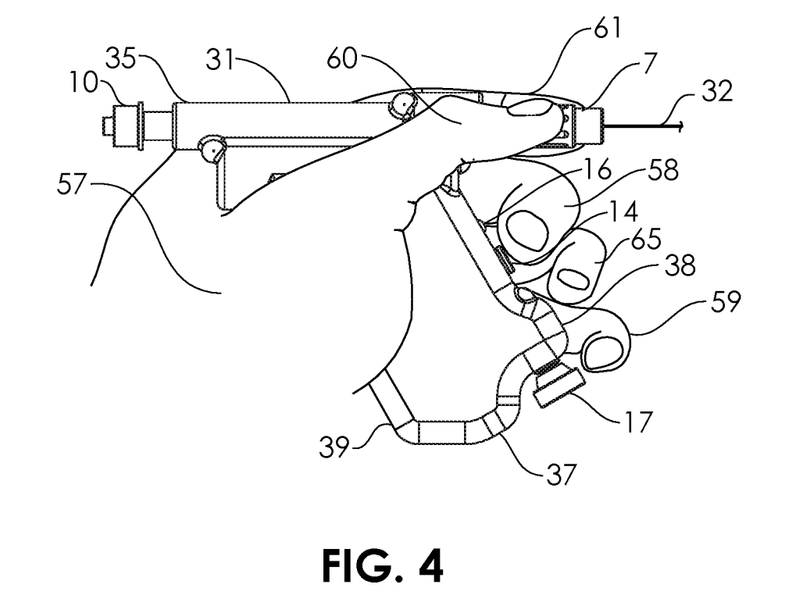
FIG. 4 is a side view of the guidewire manipulation device of FIG. 1 held in the hand of a user.

Turning to FIG. 3, the distally facing surface 38 extends at an angle $\alpha$ that is distally oriented in relation to a plane 56 cutting through the guidewire manipulation device 31 and perpendicular to the longitudinal axis 36. In some embodiments, the angle $\alpha$ may be between about 25° and about 45°, and in some embodiments, the angle $\alpha$ may be between about 30° and about 40°. In some embodiments, the angle $\alpha$ may be about 35°. At these values of angle $\alpha$, the user is able to grip the handle 37 of the guidewire manipulation device 31 while the fingers of the user's gripping hand maintain easy access to the controls 43 of the guidewire manipulation device 31. The location of the chuck 7 (and thus the location of placement of the guidewire 32) towards the top of the housing 33, above the handle 37, allows the guidewire 32 to pass through the guidewire manipulation device 31 and the user's hand without interruption. The location of the controls 43 below the longitudinal axis 36 is another factor that gives the user easy access to the controls with one or more fingers of the hand that is gripping the handle 37. As an example, in FIG. 4, the user's hand 57 is shown grasping the handle 37. In this position, the activation button 14 is easily accessible with the middle finger 58 of the user's hand 57, while at the same time the control knob 17 is easily accessible with the pinky 59 of the user's hand 57. Thus, without regripping the handle 37, the user may continually turn the motor 11 on and off as needed by pushing the activation button 14 with the middle finger 58 while also changing the rotational pattern and/or increasing or decreasing the speed of the motor 11 by turning the control knob 17 in one direction or the other with the pinky 59. Alternatively, the control knob 17 may be turned using the thumb 60 and pinky 59 together, or the thumb 60 and ring finger 65 together. The location of the chuck 7 distal to the housing 33, or distal to at least the majority of the housing 33, and distal to the handle 37, enables a user to have easy access for providing manual input to the chuck 7 with one or more fingers of the hand that is gripping, supporting, or cradling the handle 37. The user may also be able to reach distally of the chuck 7 and actually grip the guidewire 32 directly with one or more fingers of the hand, to manually stop or slow the rotation of the guidewire 32 while the housing 33 is supported by the hand of the user, or to initiate rotation or increase rotation speed of the guidewire 32. The handle 37 also allows the user leverage on the guidewire, in case it needs to be pushed or pulled.

Also shown in FIG. 4 is the feature of manual rotational control by one or more fingers of the hand 57 of the user.

With the user's hand 57 in the same gripping position, the thumb 60 and the index finger 61 are located on substantially opposite sides of the gripping portion 62 of the chuck 7. With the guidewire 32 actively being rotated by the motor 11, the user may use both the thumb 60 and the index finger 61 together to place substantially opposite normal forces on the chuck 7, for example, on the gripping portion 62, in order to slow down the rotation of the guidewire 32, or even to stop the rotation of the guidewire 32. The user may even use the thumb 60 and the middle finger 58 instead of the thumb 60 and index finger 61. In some cases, the user may even use the thumb 60, index finger 61, and the middle finger 58 together. The motor 11 and/or gear module 45 can be configured to stall at a particular stall torque. For example, the stall torque of the motor 11 (or motor 11 and gear module 45) may be a torque that can be overcome by pressure that can be applied by most users, using one or more of their fingers on the chuck 7. In some embodiments, the overall stall torque is configured to be about 24 ounce-inches or less. In other embodiments, the overall stall torque is configured to be between about 0.1 ounce-inches and about 24 ounce-inches (about $7.06 \times 10^{-4}$ newton-meter to about 0.169 Newton-meter). In other embodiments, the overall stall torque is configured to be between about 1.5 ounce-inches and about 24 ounce-inches (about 0.010 newton-meter to about 0.169 Newton-meter). The ability of the user to manually override the guidewire manipulation device 31 at any time increases the overall safety profile of the device. For example, in the event of a circuit board failure or motor failure, of the guidewire 32 is still being rotated, the user is nevertheless able to manually stop guidewire rotation. This is a particularly important feature, because scenarios may occur wherein any further rotation of the guidewire 32 within a blood vessel or other location in a patient's body could potentially cause damage. By having the motor 11 on at all times and slowing, stopping, and/or starting and speeding up the rotation of the guidewire by manual input alone, the procedure is very much in the control of a single hand of the user. Additionally, the procedure is simplified, as the circuit board 21 remains simply in an "on" mode, and is not required for the manual speed changes. The user is able to switch back and forth between motorized control and manual control at will. The fingers of the user are always in position to manipulate the chuck 7 (to change the speed of the guidewire) and to operate any of the controls 43, without any need to change the grip on the handle 37 of the guidewire manipulation device 31. The same grip may be maintained while advancing or retracting the guidewire in the patient.

Though the chuck 7 may be easily gripped by both the thumb 60 and the index finger 61, alternatively, the user may choose to apply a one-sided normal force on the chuck 7 from only one of the thumb 60 or index finger 61 to slow or stop the motor 11 rotation. The gripping portion 62 is shown with a series of circumferentially-arrayed, radially-protruding, longitudinally-lying ribs. However, in alternative embodiments, the gripping portion 62 may be knurled or comprise a series of bumps. In other alternative embodiments, the gripping portion 62 may comprise a tacky surface, which, due to its relatively high coefficient of friction, may even be a smooth cylindrical shape.

Returning to FIG. 3, proximally facing surface 39 is shown extending at an angle β that is also distally oriented in relation to plane 56. Alternatively, the proximally facing surface 39 may be contoured in other shapes to conform to the shape of typical hands of users.

In some embodiments, the controller 46 may be configured, or configured to be programmed, such that a number of different rotation schemes are applied to the guidewire 32. These different schemes may be selected by the user by turning the control knob 17 to a different orientation or different detents. For example, the motor 11 may be commanded to rotate the guidewire 32 a certain number of turns in a first rotational direction, and then to rotate the guidewire in a certain number of turns in a second, opposite direction. In other embodiments, the motor 11 may be commanded to rotate the guidewire 32 at a series of different speeds, or at accelerating and/or decelerating speeds. For example, in a particular embodiment, the motor 11 is commanded to rotate the guidewire 32 in a first rotational direction at a first rotational speed, and then in a second, opposite rotational direction at a second rotational speed, different from the first rotational speed. In yet another embodiment, the motor 11 may be commanded to rotate the guidewire 32 in a first rotational direction at a varying rotational speed and then in a second, opposite, rotational direction at a varying rotational speed. The varying rotational speed may include: a speed that is increasing with time; a speed that is decreasing with time; or a speed that includes different finite speeds which begin and end at different time periods. Certain body tissue characteristics or geometry may respond better to one speed more than another, and so the varying of speeds may aid in finding the more effective speed for a particular tissue and/or geometry condition. The same can be said about different rotational directions and/or numbers of rotations. Additional designs and schemes for rotating and/or longitudinally actuating a guidewire which may be incorporated into any of the embodiments described herein can be found in U.S. Pat. No. 9,119,941, entitled "Method and Apparatus for Manipulating a Surgical Guidewire," which issued to Rollins et al. on Sep. 1, 2015, and U.S. Pat. No. 9,119,942, entitled "Guidewire Manipulation Device," which issued to Rollins et al. on Sep. 1, 2015, the contents of each which are hereby incorporated by reference in their entirety for all purposes.

In some embodiments, the controller 46 may be configured to, or configured to be programmed to direct the motor 11 to rotate the guidewire 32 clockwise for about 0.2 seconds, and then switch directions and rotate the guidewire 32 counter-clockwise for about 0.2 seconds. The motor 11 may be commanded by the controller 46 to continuously repeat this pattern. In some embodiments, the controller 46 may be configured to, or configured to be programmed to direct the motor 11 to rotate the guidewire 32 clockwise for about 1.0 second, and then switch directions and rotate the guidewire 32 counter-clockwise for about 1.0 second. The motor 11 may be commanded by the controller 46 to continuously repeat this pattern. In other embodiments, the controller 46 may be configured to, or configured to be programmed to direct the motor 11 to rotate the guidewire 32 only a certain number of degrees in each direction. For example, about 180 degrees in a first direction and then about 180 degrees in the opposite direction. The motor 11 may be commanded by the controller 46 to continuously repeat this pattern. In other embodiments, the controller 46 may be configured to, or configured to be programmed to direct the motor 11 to rotate the guidewire 32 between about one-quarter and about thirty-eight full rotations in a first direction and then between about one-quarter rotation and about thirty-eight full rotations in the opposite direction. The motor 11 may be commanded by the controller 46 to continuously repeat this pattern. In other embodiments, the controller 46 may be configured to, or configured to be programmed to direct the motor 11 to rotate the guidewire 32 between about six and about ten full rotations in a first direction and then between about six and about ten full rotations in the opposite direction. The motor 11 may be commanded by the controller 46 to continuously repeat this pattern. The circuit board 21 may comprise an H-bridge to switch the motor polarity, and thus the motor rotational direction between a first and second direction (e.g., forward and reverse). Any number of different patterns or routines may be programmed into or programmable into the controller 46. In some embodiments, settings may be available in discrete choices, for example, low, medium, or high. In other embodiments, the settings may be adjusted through a continuous range in the particular parameter or parameters.

In some embodiments, the guidewire manipulation device 31 may include elements that are coupled to any of the rotatable portions (chuck 7, drive tube 2, etc.) which allow for rotation in a first direction, but not in a second, opposite direction. For example, any of these rotatable elements may be coupled to a free wheel, a clutch, or a ratchet.

The reverse gun handle shape of the handle 37 and the location of the controls 43 enable the guidewire manipulation device 31 to be comfortably used with a single hand. The textured surface of the gripping portion 62 of the chuck 7 may be configured, for example, so that one of the ribs has a larger radial protrusion dimension than the other ribs, or in other embodiments, so that there is only one radially-protruding rib. This configuration allows tactile feedback to the user, or more specifically, knowledge of about how fast the guidewire is being rotated from feel only, without having to look at the chuck 7, or at any display. The user, thus, does not have to continually watch the guidewire manipulation device 31 while using it.

Figure 5:
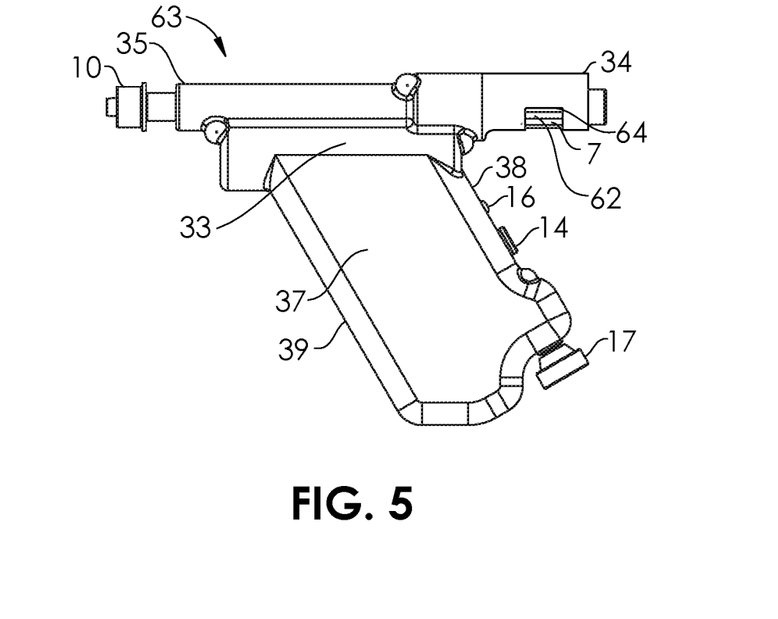
FIG. 5 is a side view of a guidewire manipulation device according to a second embodiment of the disclosure.
Figure 6:
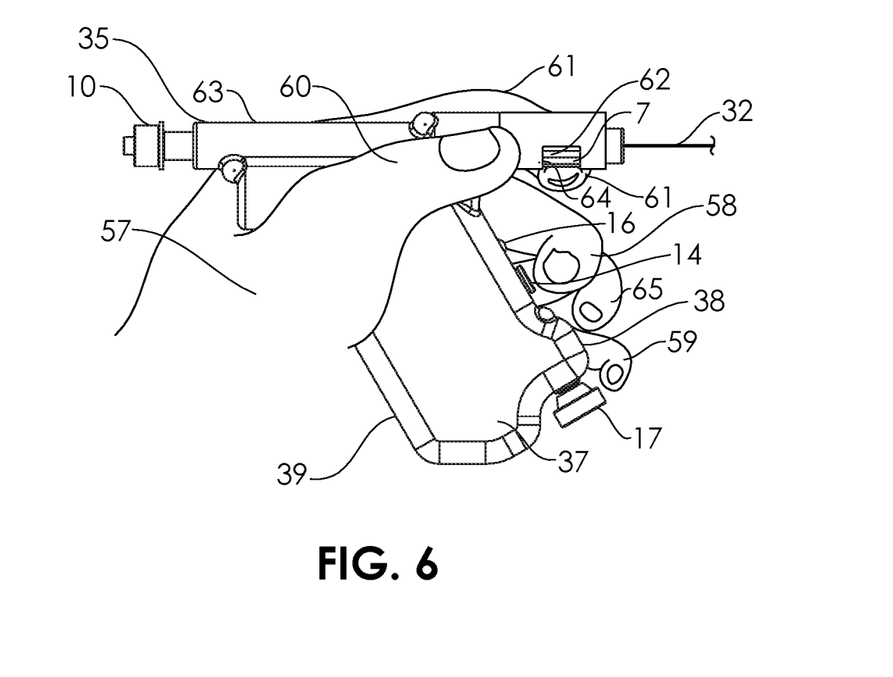
FIG. 6 is the guidewire manipulation device of FIG. 5 held in the hand of a user.
Figure 7:
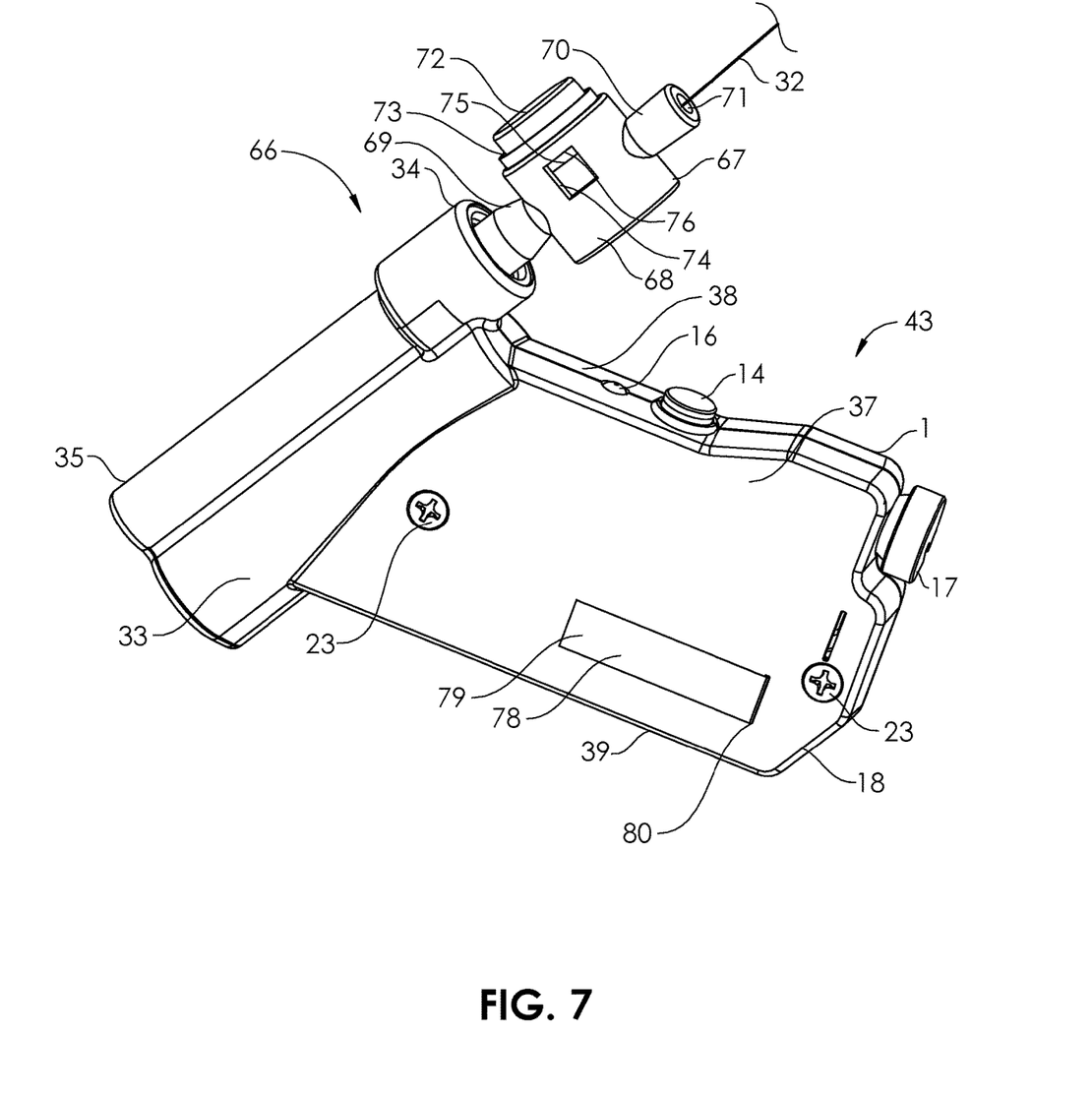
FIG. 7 is a perspective view of a guidewire manipulation device according to a third embodiment of the disclosure.

FIGS. 5 and 6 illustrate a guidewire manipulation device 63 that includes most of the features and utility of the guidewire manipulation device 31 of FIGS. 1-4, however, the chuck 7 of the guidewire manipulation device 63 is at least partially within the housing 33. A window 64 in the housing 33 exposes a portion of the gripping portion 62 of the chuck 7, so that, while the user is gripping the handle 37, the gripping portion 62 may be touched by a single finger of the user's hand 57, including the index finger 61, the middle finger 58, the pinky 59, the ring finger 65, or in some cases, even the thumb 60. It should be noted that the though the word "gripping" is being used in the name of the gripping portion 62 of the guidewire manipulation device 63 of FIGS. 5 and 6, in some embodiments the window 64 may be configured in a way that a typical user cannot actually grip two points on the gripping portion 62 (e.g., with two different fingers). However, by placing a normal force (using applied finger pressure) on the gripping portion 62 of the chuck 7, as the index finger 61 is shown being done by the index finger 61 in FIG. 6, the user may still slow or stop the rotation of a guidewire 32 being rotated by the motor 11. Additionally, the user may start rotation or speed up rotational speed of a guidewire 32 that is being rotated by the motor 11, or is not being rotated by the motor 11. Thus, the chuck 7 of the guidewire manipulation device 63 of the embodiment of FIGS. 5-6 can be controlled by finger-based manipulation, much in the same manner as the chuck 7 of the guidewire manipulation device 31 of the embodiment of FIGS. 1-4. In some embodiments, if the window 64 is configured large enough, two or more fingers may have access to place a normal force on the gripping portion 62 of the chuck 7, either in an opposing manner, or together in the same direction (substantially parallel).

FIGS. 7-10 illustrate a guidewire manipulation device 66 that includes most of the features and utility of the guidewire manipulation device 31 of FIGS. 1-4, however, several components are different. A chuck 67 is configured to grip the guidewire 32 and to be rotated by the motor 11 in order to rotate the guidewire 32, as with the chucks 7 in the embodiments of FIGS. 1-4 and FIGS. 5-6. An internal diameter at the first end 69 of the chuck 67 may be bonded (adhesive, epoxy) to an external diameter of the drive tube 2. The drive tube may comprise stainless steel or other substantially rigid materials. The chuck 67 may comprise any of the gripping configurations and mechanisms of embodiments of a torque device as described in U.S. Pat. No. 7,972,282, entitled "Torque Device for a Medical Guidewire," which issued to Clark et al. on Jul. 5, 2011, the contents of which is hereby incorporated by reference in its entirety for all purposes. The chuck 67 includes a body 68 having a first end 69 and a second end 70. A cavity 71 passes through the body 68 and is configured for the placement of a guidewire 32 (or other elongate medical device). An actuator 72 is telescopically carried within a channel 73, and is spring-loaded (or otherwise biased), so that, when depressed (e.g., in the manner of a push button), a guidewire may pass through, and when released, the guidewire is gripped, as the actuator moves toward its biased position. Thus, a guidewire 32 may be engaged with the chuck 37 or disengaged with the chuck by simply pushing the actuator 72 and removing or inserting the guidewire 32. The actuator 72 may be maintained within the channel 73 of the body 68 (so that it does not fall out) by a catch 75 on the side of the actuator 72, which abuts a ledge 76 in an opening 74 in the body 68. In alternative embodiments a similar chuck 67 may be used which instead of having an actuator 72 that is pushed in order to insert the guidewire 32 and released in order to grip the guidewire 32, instead has an actuator the is pushed in order to grip the guidewire 32, or in other embodiments, and actuator that is pulled in order to grip the guidewire 32. In some embodiments, an additional sleeve, such as a silicone sleeve, is secured to the end of the drive tube 2, in place of the chuck 67. The silicone sleeve rotates in unison with the drive tube and has an internal diameter that is configured to snugly fit around the exterior of a variety of different torque devices (torquers), including any off-the-shelf torque device. Thus, many different torque devices may be used in place of the chuck 67 to rotate the guidewire 32. Instead of a sleeve, a standard chuck or graspers may be used, or a cavity having a set screw, in order to secure one or more torque device to the drive tube 2.

The drive tube 2 is maintained on one end by a support cap 77, which may or may not be configured to include a luer. A safety element (not shown) may be carried on the handle 37 and may be electrically coupled to the circuit board 21. The safety element may comprise an electrode or coupled surface may serve to couple a terminal of the circuit board 21 to the hand 57 of the user. The safety element may cover a portion of both sides of the handle 37 so that the hand 57 will contact the activation strip whether it is a left hand or a right hand. In some embodiments, the safety element may be capacitive, and in other embodiments, the safety element may be conductive. In some embodiments, the controller 46 may be configured to not allow the on/off switch signal to be received or transmitted unless the safety element is coupled and/or grounded (to the user).

Figure 8:
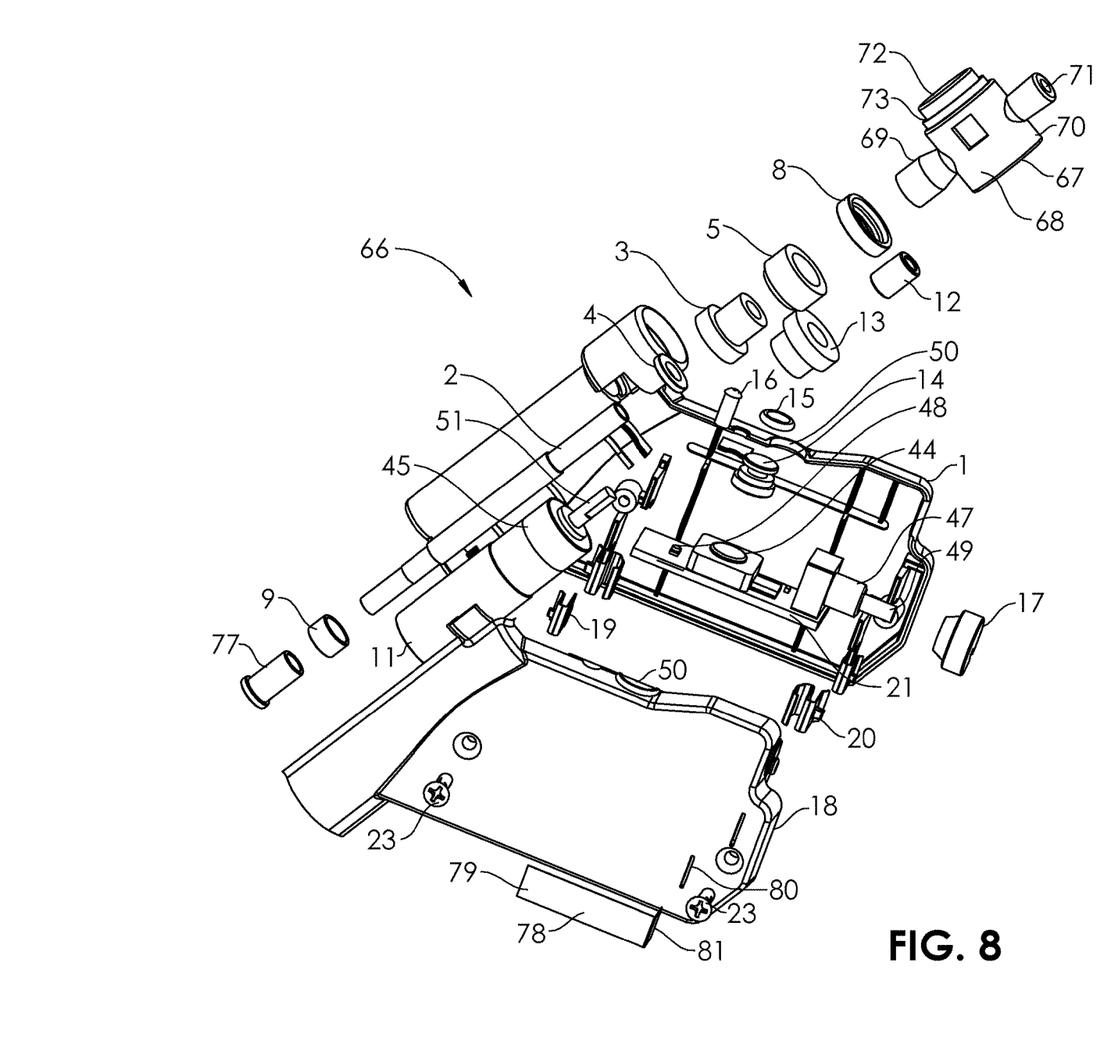
FIG. 8 is an exploded view of the guidewire manipulation device of FIG. 7.
Figure 9:
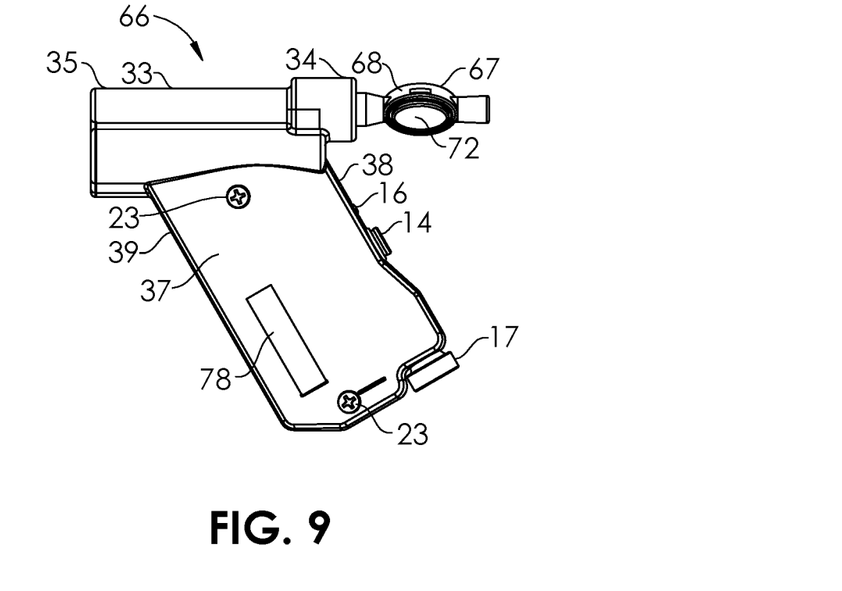
FIG. 9 is a side view of the guidewire manipulation device of FIG. 7.
Figure 10:
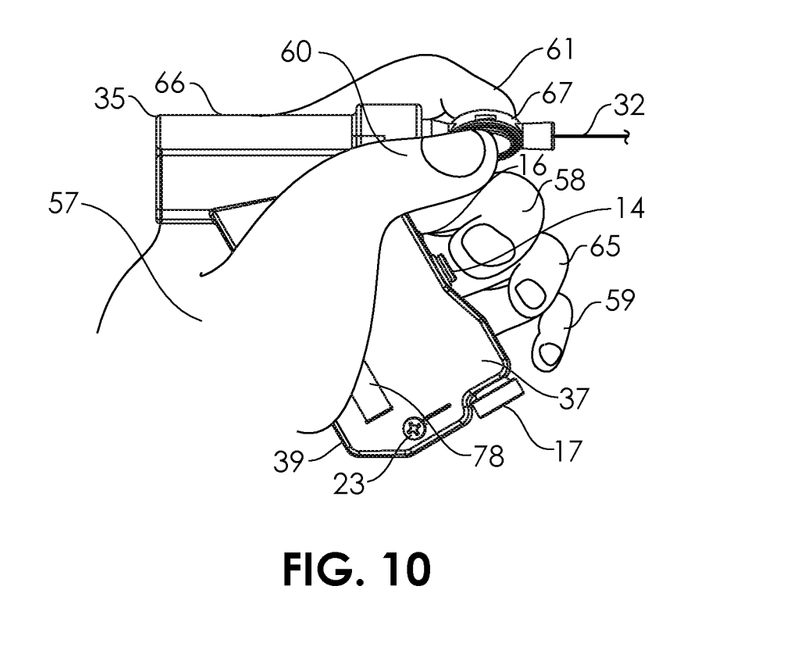
FIG. 10 is a side view of the guidewire manipulation device of FIG. 7 held in the hand of a user.

An activation strip 78 has a first end 79 that extends out of the second housing half 18 through a slit 80 and a second end 81 that is held between and end (e.g., terminal) of one or more of the batteries 25 (not visible in FIG. 8, see FIG.

2) and one or more of the contacts 19, 20. Prior to using the guidewire manipulation device 66, the user grips the first end 79 of the activation strip 78 and applies a tensile force in order to remove the activation strip 78 completely, thus allowing the end or terminal of the battery 25 to directly contact the contact(s) 19, 20. The activation strip 78 comprises a dielectric material, such as polyimide (e.g., Kapton®) and may have a relatively high material strength. Thus, the activation strip 78 functions to prevent the batteries 25 from discharging while the guidewire manipulation device 66 is on the shelf or stored prior to being used.

The shape of the chuck 67 has a non-round cross-section and thus allows tactile feedback to the user while it is being rotated by the motor 11. The user, thus, does not have to continuously, or continually, monitor the guidewire manipulation device 66 visually while using the guidewire manipulation device 66 in a medical procedure. Thus the user is able to focus on other aspects of the medical procedure that are important. These may include, patient vital signs (body temperature, pulse rate, respiration rate, blood pressure, etc.) or other characteristics that indicate the effectiveness of the treatment (amount of thrombus removed, fluoroscopic or radiographic image, etc.). In additional, no rotational counter (encoder, etc.) is required to provide rotational feedback during the procedure as the non-round external contour of the chuck 67 provides simple indication of the number of turns and of the general rate of rotation.

When the guidewire manipulation device 31, 63, 66 is used in a back-and-forth mode, wherein the guidewire is turned by the motor 11 in oscillations of a particular number in each direction, the user is also able to visually monitor the type or number of oscillations by viewing the non-round external contour of the rotating chuck 67. The user may even choose to give manual input to slow, speed up, or stop the rotation of the chuck 67 and guidewire 32 in one rotational direction, and not the other. This may be useful in certain situations, such as when the guidewire 32 or other elongate medical device is being tracked around a corner or tortuosity.

Any of the chucks 7, 67 may be replaced with other guidewire torque devices, including pin vice-type guidewire torquers, sliding friction guidewire torquers, or soft grip devices such as the H₂O Torq™ Device sold by Merit Medical Systems, Inc. of South Jordan, Utah, USA. The chucks 7, 67 may be configured to grip guidewires that are uncoated, or coated with hydrophilic coatings or lubricants such as silicone or silicone oil.

While embodiments have been shown and described, various modifications may be made without departing from the scope of the inventive concepts disclosed herein.

What is claimed is:

1. A guidewire manipulation device configured for single hand use comprising:
   a housing configured to be supported by a hand of a user, the housing including a distal end, a proximal end, and a longitudinal axis extending therebetween, the housing comprising a passage extending from the distal end of the housing to the proximal end of the housing, the passage configured for a guidewire to be placed therethrough;
   a chuck rotationally coupled to the housing, the chuck having a locked mode configured to engage the guidewire such that rotation of the chuck causes corresponding rotation of the guidewire, while maintaining the longitudinal position of the guidewire in relation to the housing, the chuck further having an unlocked mode wherein the chuck is configured to not cause rotation of the guidewire;
   a motor carried by the housing and configured to drive rotation of the chuck, the motor having a stall torque, the motor configured to be switched between an on condition and an off condition;
   a hand grip extending from the housing in a generally radial direction in relation to the longitudinal axis; and
   an engagement interface carried on an external portion of the chuck such that the engagement interface maintains a particular longitudinal position in relation to the hand grip when the chuck is in the locked mode, wherein the engagement interface, the hand grip, and the stall torque are configured to collectively allow one or more fingers of the hand of the user to apply a force to the engagement interface sufficient to stop or slow the rotation of the chuck while the hand grip is being gripped by the hand of the user and while the motor is in the on condition and rotationally driving the chuck.

2. The guidewire manipulation device of claim 1, wherein the engagement interface is configured to allow one or more fingers of the hand of the user to manually rotate the guidewire when the hand grip is gripped by the hand of the user and the chuck is not being driven by the motor.

3. The guidewire manipulation device of claim 1, further comprising a drive system comprising the motor, wherein the drive system is configured to permit rotation of the chuck in a first rotational direction and to inhibit the rotation of the chuck in a second rotational direction, the second rotational direction opposite the first rotational direction.

4. The guidewire manipulation device of claim 1, wherein the engagement interface has a non-circular cross-section.

5. The guidewire manipulation device of claim 4, wherein the engagement interface includes one or more protrusions.

6. The guidewire manipulation device of claim 1, further comprising a drive system comprising the motor, wherein the drive system is configured to apply alternating clockwise motion and counter-clockwise motion to the chuck.

7. The guidewire manipulation device of claim 1, wherein the stall torque of the motor is between about 0.1 ounce-inches and about 24 ounce-inches.

8. The guidewire manipulation device of claim 1, further comprising an activation member carried by the hand grip and configured to initiate operation of the motor when activated by the hand of the user while the hand grip is gripped by the hand of the user.

9. The guidewire manipulation device of claim 1, wherein the hand grip includes a distally facing surface and a proximally facing surface, the distally facing surface having a first end and a second end, wherein the first end of the distally facing surface is closer to the longitudinal axis than the second end of the distally facing surface, and wherein the first end of the distally facing surface corresponds with a first point along the longitudinal axis and the second end of the distally facing surface corresponds with a second point the longitudinal axis, the first point proximal to the second point.

10. The guidewire manipulation device of claim 1, wherein the hand grip includes a distally facing surface and a proximally facing surface, the distally facing surface having a first portion and a second portion, wherein the first portion is closer to the longitudinal axis than the second portion, and wherein the distally facing surface sweeps distally from the first portion to the second portion at an angle of between about 25° and about 45°.

11. The guidewire manipulation device of claim 10, wherein the distally facing surface sweeps distally from the first portion to the second portion at an angle of between about 30° and about 40°.

12. The guidewire manipulation device of claim 9, wherein the proximally facing surface has a first end and a second end, wherein the first end of the proximally facing surface is closer to the longitudinal axis than the second end of the proximally facing surface, and wherein the first end of the proximally facing surface corresponds with a third point along the longitudinal axis and the second end of the proximally facing surface corresponds with a fourth point the longitudinal axis, the third point proximal to the fourth point.

13. A method for manipulating an elongate medical device, comprising:
providing a guidewire manipulation device configured for single hand use comprising:
a housing configured to be supported by a hand of a user, the housing including a distal end, a proximal end, and a longitudinal axis extending therebetween, the housing comprising a passage extending from the distal end of the housing to the proximal end of the housing, the passage configured for a guidewire to be placed therethrough;
a chuck rotationally coupled to the housing, the chuck having a locked mode configured to engage the guidewire such that rotation of the chuck causes corresponding rotation of the guidewire, while maintaining the longitudinal position of the guidewire in relation to the housing, the chuck further having an unlocked mode wherein the chuck is configured to not cause rotation of the guidewire;
a motor carried by the housing and configured to drive rotation of the chuck, the motor having a stall torque, the motor configured to be switched between an on condition and an off condition;
a hand grip extending from the housing in a generally radial direction in relation to the longitudinal axis; and
an engagement interface carried on an external portion of the chuck such that the engagement interface maintains a particular longitudinal position in relation to the hand grip when the chuck is in the locked mode, wherein the engagement interface, the hand grip, and the stall torque are configured to collectively allow one or more fingers of the hand of the user to apply a force to the engagement interface sufficient to stop or slow the rotation of the chuck while the hand grip is being gripped by the hand of the user and while the motor is in the on condition and rotationally driving the chuck;
securing an elongate medical device to the chuck;
grasping the guidewire manipulation device in a first hand; and
causing the elongate medical device to change a rotation speed by input to the engagement interface from one or more fingers of the first hand.

14. The guidewire manipulation device of claim 1, further comprising:
a control carried by the hand grip, the control configured to be manipulated by one or more fingers of the hand of the user while the hand grip is gripped by the hand of the user.

15. The guidewire manipulation device of claim 14, wherein the control is configured to perform at least one of: selecting two or more rotational settings or changing rotational speed.

16. The guidewire manipulation device of claim 1, wherein the stall torque of the motor is between about 1.5 ounce-inches and about 24 ounce-inches.

17. The guidewire manipulation device of claim 1, further comprising:
a control carried by the hand grip, the control configured to be manipulated by one or more fingers of the hand of the user to switch the guidewire manipulation device between manually-operated rotation of the chuck and motorized rotation of the chuck.

18. The guidewire manipulation device of claim 1, wherein the engagement interface comprises a tacky surface.

19. The guidewire manipulation device of claim 1, wherein the housing includes an opening substantially transverse to the longitudinal axis, and located between the distal and proximal ends of the housing, and wherein the chuck is located within the housing such that at least a first portion of the engagement interface is covered by the housing and at least a second portion of the engagement interface is uncovered by the transverse opening in the housing.

20. The method of claim 13, wherein the causing step comprises slowing down the rotation of the medical device by contacting the engagement interface with the one or more fingers of the first hand while the hand grip is being grasped by the first hand and the chuck is being rotated by the motor.

21. The method of claim 20, further comprising allowing the rotation of the medical device to speed up by changing the pressure of the engagement of the one or more fingers of the first hand with the engagement interface.

22. The method of claim 13, wherein the causing step comprises stopping the rotation of the medical device by contacting the engagement interface with the one or more fingers of the first hand while the hand grip is being grasped by the first hand and the chuck is being rotated by the motor.

23. The method of claim 22, further comprising allowing the medical device to begin to rotate again by changing the pressure of the engagement of the one or more fingers of the first hand with the engagement interface.

24. The method of claim 13, wherein the causing step comprises manually rotating the medical device by contacting the engagement interface with the one or more fingers of the first hand and placing a torque on the chuck while the hand grip is being grasped by the first hand and the chuck is not being rotated by the motor.

25. The method of claim 9, wherein the distally facing surface is configured for wrapping two or more fingers of the user's hand therearound.

26. The method of claim 1, wherein the chuck comprises a bias configured to releasably grip the guidewire.

\* \* \* \* \*

UNITED STATES PATENT AND TRADEMARK OFFICE
CERTIFICATE OF CORRECTION

PATENT NO. : 11,285,300 B2
APPLICATION NO. : 15/235920
DATED : March 29, 2022
INVENTOR(S) : Brandon M. Felkins et al.

Page 1 of 1

It is certified that error appears in the above-identified patent and that said Letters Patent is hereby corrected as shown below:

In the Claims

Column 12, Claim 9, Line 9: insert -- along -- after "with a second point"

Column 13, Claim 12, Line 8: insert -- along -- after "with a fourth point"

Signed and Sealed this
Twenty-sixth Day of July, 2022

Katherine Kelly Vidal
*Director of the United States Patent and Trademark Office*